(12) United States Patent
Chen et al.

(10) Patent No.: US 7,645,904 B2
(45) Date of Patent: Jan. 12, 2010

(54) PURIFICATION OF BIS(THIOHYDRAZIDE AMIDES)

(75) Inventors: Shoujun Chen, Bedford, MA (US); Zhi-Qiang Xia, Acton, MA (US); Elena I. Kostik, Arlington, MA (US); Keizo Koya, Chestnut Hill, MA (US); Lijun Sun, Harvard, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 293 days.

(21) Appl. No.: 11/901,265

(22) Filed: Sep. 14, 2007

(65) Prior Publication Data

US 2008/0146842 A1    Jun. 19, 2008

Related U.S. Application Data

(60) Provisional application No. 60/844,776, filed on Sep. 15, 2006.

(51) Int. Cl.
C07C 327/48 (2006.01)
C07C 327/42 (2006.01)
C07C 255/66 (2006.01)

(52) U.S. Cl. .................... 564/74; 564/78; 558/414

(58) Field of Classification Search ............... 558/414; 564/74, 78
See application file for complete search history.

(56) References Cited

U.S. PATENT DOCUMENTS

| | | | |
|---|---|---|---|
| 4,012,360 A | 3/1977 | Schwarzenbach et al. |
| 4,822,777 A | 4/1989 | Abra |
| 5,840,746 A | 11/1998 | Ducharme et al. |
| 6,013,836 A | 1/2000 | Hsu et al. |
| 6,172,108 B1 | 1/2001 | Vega et al. |
| 6,172,188 B1 | 1/2001 | Thastrup et al. |
| 6,235,787 B1 | 5/2001 | Broadhurst et al. |
| 6,365,745 B1 | 4/2002 | Matsui et al. |
| 6,399,659 B2 | 6/2002 | Usui et al. |
| 6,435,787 B1 | 8/2002 | John |
| 6,455,515 B2 | 9/2002 | Gypser et al. |
| 6,656,971 B2 | 12/2003 | Wu et al. |
| 6,703,426 B1 | 3/2004 | Miles et al. |
| 6,762,204 B2 | 7/2004 | Koya et al. |
| 6,800,660 B2 | 10/2004 | Koya et al. |
| 6,825,235 B2 | 11/2004 | Chen et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 2002/0198160 A1 | 12/2002 | Everitt et al. |
| 2004/0022869 A1 | 2/2004 | Chen et al. |
| 2004/0225016 A1 | 11/2004 | Koya et al. |
| 2006/0142386 A1 | 6/2006 | Barsoum |
| 2006/0142393 A1 | 6/2006 | Sherman et al. |
| 2006/0270873 A1 | 11/2006 | Chen et al. |
| 2007/0088057 A1 | 4/2007 | Lunsmann et al. |
| 2008/0089950 A1 | 4/2008 | Chen et al. |
| 2008/0118562 A1 | 5/2008 | Koya |
| 2008/0119440 A1 | 5/2008 | Koya |
| 2008/0146842 A1 | 6/2008 | Chen et al. |
| 2008/0176828 A1 | 7/2008 | Williams et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0042991 A1 | 2/2009 | Barsoum et al. |

FOREIGN PATENT DOCUMENTS

| | | |
|---|---|---|
| DE | 2037257 | 2/1972 |
| FR | 2097737 | 4/1972 |
| GB | 1 272 920 | 5/1972 |
| JP | 50-91056 | 7/1975 |
| JP | 63-267752 | 11/1988 |
| JP | 07-165693 | 6/1995 |
| JP | 10-501215 | 2/1998 |
| WO | WO 94/10995 A1 | 5/1994 |
| WO | WO 99/34796 A1 | 7/1999 |
| WO | WO 03/006428 A1 | 1/2003 |
| WO | WO 03/006429 A1 | 1/2003 |
| WO | WO 03/006430 A1 | 1/2003 |

(Continued)

OTHER PUBLICATIONS

Chuiguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr, Khim. Zhurn.* 48:520 (1984).
"Remarks" paper as submitted by Applicant's Attorney.
Stalteri, M.A. et al., "Site-specific conjugation and labelling of prostate antibody 7E11C5.3 (CYT-351) with technetium-99m," *European Journal of Nuclear Medicine* 24(6):651-654, (1997).
Twomey, D., "Anticancer Agents-IX. Derivatives of Pyridine, Pyridazine and Phthalazine," *Proceedings of the Royal Irish Academy*, vol. 74, Sect. B:37-52,(1974).
Schwarz et al., CA77:48081, 1972.
Rupp, Walter, CA76:126992, 1972.

(Continued)

*Primary Examiner*—Peter G O'Sullivan
(74) *Attorney, Agent, or Firm*—Foley & Lardner LLP; Steven G. Davis

(57) ABSTRACT

Disclosed herein are methods of purifying a bis(thio-hydrazide amides) compounds of the following structural formula:

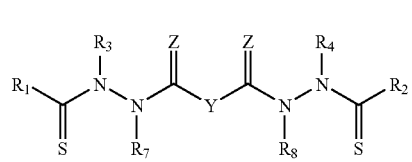

wherein $R_1$, $R_2$, $R_3$, $R_4$, $R_7$, $R_8$, Z, and Y are defined herein.

29 Claims, No Drawings

FOREIGN PATENT DOCUMENTS

| WO | WO 03/047524 A2 | 6/2003 |
|---|---|---|
| WO | WO 2004/064826 A1 | 8/2004 |
| WO | WO 2006/009940 A1 | 1/2006 |
| WO | WO 2006/033913 A2 | 3/2006 |
| WO | WO 2006/055747 A2 | 5/2006 |
| WO | WO 2006/113493 A2 | 10/2006 |
| WO | WO 2006/113572 A1 | 10/2006 |
| WO | WO 2006/113695 A1 | 10/2006 |
| WO | WO 2006/124736 A2 | 11/2006 |
| WO | WO 2007/021881 A2 | 2/2007 |
| WO | WO 2008/024298 A1 | 2/2008 |
| WO | WO 2008/024299 A2 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033494 A2 | 3/2008 |
| WO | WO 2008/082579 A1 | 7/2008 |
| WO | WO 2009/020631 A2 | 2/2009 |

OTHER PUBLICATIONS

Barry, V. C. et al., "Anticancer Agents III. Synthesis and Anticancer Activity of Some Bis-Thiosemicarbazones and Thoiosemicarbazides," *Proc. R.I.A.* 65:309-324 1967).

O'Callaghan, C. N., "Anticancer Agents—X. Cyclísation of 1-Acyl-4-Alkylthiosemicarbazide Derivatives to 1,2,4-Triazoline-3-Thiones in the Presence of Hydrazine," *Proc. R.I.A.* 74:455-461 (1974).

Molina, P. et al., XP-01118868, "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles Containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s*, 5:1159-1166 (1991).

Molina, P. et al., XP-001118802, "Preparation of a Novel Type of Ligands Incorporating Two or Three 1,3,4-Thiadiazole Units," *Heterocycles*, 36(6): 1263-1278 (1993).

Merlin, J,-L. et al., "In vitro Comparative Evaluation of Trastuzumab (Herceptin®) Combined with Paclitaxel (Taxol®) or Docetaxel (Taxotere®) in HER2-Expressing Human Breast Cancer Cell Lines," *Annals of Oncology*, vol. 13: 1743-1748 (2002).

Asahi Chemical Ind. K.K. Abstract of Japanese Patent No. 50-91056, Accession No.: 47521Y/27 (1975).

Bräuniger, H., "Hydrazide und Hydrazidderivate von Dicarbonsäuren," Pharmaceutical-Chemical Institute of University of Rostock, Supplied by the "British Library," *Pharmazie*, 25(5-6): 279-283 (1970).

Al-Talib, M. et al., "Diacyl Acid Dihydrazides," *Magnetic Resonance in Chemistry*, 28: 1072-1078 (1990).

Chuyguk, V.A., and Nemazanyi, A.G., "Mesoionic Methine Dyes of Biquaternary Salts Of Diheteroaryl Methanes—Derivatives Of 1, 3, 4—oxa (thia) Diazoles and 1, 2, 4—Triazoles," *Kiev. Gos. Univ., Kiev, USSR, Ukrainskii Khimicheskii Zhurnal, Russian Edition*, 50(5):519-524 (1984). Abstract, Accession No. 1984:630420, HCAPLUS Database.

Barrett, William G. and McKay, Donald, "Decomposition and Cycloaddition Reactions of Some Bis(azodicarbonyl) Compounds," *Journal of Chem. Soc.*, (4): 1046-1052 (1975).

Mitsui Toatsu Chem, Inc., Abstract of Japanese Patent No. 308024, published Dec. 25, 1986. From Derwent Publications Ltd.

Honshu Paper Mfg. Co. Ltd, Abstract of Japanese Patent No. 182050, published Feb. 13, 1996.

Brittain et al., in *Polymorphism in Pharmaceutical Solids*, (NY: M. Dekker), vol. 95, pp. 348-361 (1999).

Rao et al., "Combination of Paclitaxel and Carboplatin as Second-Line Therapy for Patients with Metastatic Melanoma," *Cancer*, vol. 106, No. 2: 375-382 (2006).

Goodman & Gilman's, The Pharmacological Basis of Therapeutics, Ninth Edition, (1996), Section X, Calabresi et al., pp. 1225-1232.

Gura et al., "Systems for Identifying New Drugs are Often Faulty," *Science*, 1997, 278: 1041-1042.

Johnson et al., "Relationships Between Drug Activity in NCI Preclinical in vitro and in vivo Models and Early Clinical Trials," *British J. of Cancer*, 2001, 84(10): 1424-1431.

Sausville et al., "Contributions to Human Tumor Xenografts to Anti-cancer Drug Development," *Cancer Research*, 2006, vol. 66, pp. 3351-3354.

Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.

"The Merck Manual," Chapter 14: Principles of Cancer Therapy, 1999 Merck Research Laboratories, pp. 987-995 (1999), XP002477370.

Wust, P. et al., "Hyperthermia in Combined Treatment of Cancer," *The Lancet Oncology*, 3(8): 487-497 (Aug. 2002), XP004813895.

Biagi, G. et al.,"1,5-Diarylsubstituted 1,2,3-triazoles as Potassium Channel Activators. VI," *Il Farmaco*, 59(5): 397-404 (2004), esp. p. 398.

Patani, et al., "Bioisosterism: A Rational Approach in Drug Design," Chem. Rev., 96: 3147-3176 (1996), esp. p. 3152.

Balkwill, F. et al., "Inflammation and Cancer: Back to Virchow?" *The Lancet*, 357: 539-545 (Feb. 2001).

Jacquier-Sarlin, M.R. et al., "Protective Effects of hsp70 in Inflammation," *Experientia*, 50(11-12): 1031-1038 (Nov. 1994).

Cancer, Wikipedia, http://en.wikipedia.org/wiki/Cancer (1 of 40) Aug. 2, 2008 (all pages).

Mar. 25, 2008, International Search Report, PCT/US2007/019987.

Mar. 25, 2008, Written Opinion of the International Searching Authority, PCT/US2007/019987.

U.S. Appl. No. 11/918,357, filed Apr. 13, 2006.

U.S. Appl. No. 12/221,926, filed Aug. 7, 2008.

PURIFICATION OF BIS(THIOHYDRAZIDE AMIDES)

RELATED APPLICATION

This application claims the benefit of U.S. Provisional Application No. 60/844,776, filed on Sep. 15, 2006. The entire teachings of the above application(s) are incorporated herein by reference.

BACKGROUND OF THE INVENTION

Cancer is a group of diseases that are characterized by uncontrolled cell division. This uncontrolled division can compromise the function of an organism and ultimately may cause its death.

On average, in the United States, men have a 1 in 2 lifetime risk of developing cancer and women, a 1 in 3 risk. The International Agency for Research on Cancer estimated that there were 5.3 million new cases of cancer and 3.5 million cancer deaths worldwide in 2000. In the United States, more than 1.2 million new cases were diagnosed in 2002 and more than 550,000 people died of the disease. In fact, cancer is the second leading cause of death in the United States, exceeded only by heart disease.

Many cancers are immunosensitive. Immunosensitve cancers respond to immunotherapy, i.e., agents that stimulate the immune system. Examples of immunosensitive cancers include, renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia.

Heat shock proteins (HSPs) are found in virtually all prokaryotic and eukaryotic cells where they support folding of nascent polypeptides, prevent protein aggregation, and assist transport of other proteins across membranes. The proteins in the Hsp70 family (referred to collectively as "Hsp70") play a dual role of protecting cells from lethal damage after environmental stress, on the one hand, and targeting cells for immune mediated cytolytic attack on the other hand. Increased expression of Hsp70 in the cytoplasma is known to protect a broad range of cells under stress by preventing the misfolding, aggregation and denaturation of cytoplasmic proteins and inhibiting various apoptotic pathways (Mosser, et al., Mol Cell Biol. 2000 October; 20(19): 7146-7159; Yenari, Adv Exp Med Biol, 2002, 513, 281-299; Kiang and Tsokos, Pharmacol Ther. 1998; 80(2):182-201). However, membrane-bound Hsp70 provides a target structure for cytolytic attack mediated by natural killer cells.

Cells can experience stress due to temperature; injury (trauma); genetic disease; metabolic defects; apoptosis; infection; toxins; radiation; oxidants; excess/lack of nutrients or metabolic products; and the like. For example, it is known in the art that cells damaged in the following variety of medical conditions can experience a protective effect in response to Hsp70.

Protein misfolding/aggregation conditions resulting in neurodegeneration include Alzheimers' disease (Zhang, et al., J. Neuroscience, 2004, 24(23), 5315-5321; Klettner, Drug News Perspect, 2004 17(5), 299-306); Huntington's disease (Klettner, ibid); Parkinson's disease (Auluck, et al., Science, 2002, 295(5556), 865-868); and the like. Other neurodegenerative conditions include spinal/bulbar muscular atrophy (Sobue, Nihon Shinkei Seishin Yakurigaku Zasshi, 2001, 21(1), 21-25); and familial amyotrophic lateral sclerosis (Howland, et al., Proc Nat Acad Sci USA, 2002, 99(3), 1604-1609; Sobue, ibid; Vleminck, et al., J Neuropathol Exp Neurol, 2002, 61(11), 968-974).

Ischemia and associated oxidative damage affects diverse tissues including: neurons and glia (Carmel, et al., Exp Neurol, 2004, 185(1) 81-96; Renshaw and Warburton, Front Biosci, 2004, 9, 110-116; Yenari, Adv Exp Med Biol, 2002, 513, 281-299; Kelly and Yenari, Curr Res Med Opin, 2002, 18 Suppl 2, s55-60; Lee, et al., Exp Neurol, 2001, 170(1), 129-139; Klettner, ibid; Klettner and Herdegen, Br J Pharmacol, 2003, 138(5), 1004-1012); cardiac muscle (Marber, M. S., et al. (1995) J. Clin. Invest. 95:1446-1456; Plumier, J. C., et al. (1995) J. Clin. Invest. 95:1854-1860; Radford, N. B., et al. (1996) Proc. Natl. Acad. Sci. USA 93(6): 2339-2342; Voss, et al., Am J Physiol Heart Circ Physiol 285: H687-H692, 2003); liver tissue (Doi, et al., Hepatogastroenterology. 2001 March-April; 48(38):533-40; Gao, et al. World J Gastroenterol 2004; 10(7):1019-1027); skeletal muscle (Lepore et al., Cell Stress & Chaperones, 2001, 6(2), 93-96); kidney tissue (Chen, et al., Kidney Int. 1999; 56: 1270-1273; Beck, et al., Am J Physiol Renal Physiol 279: F203-F215, 2000.); pulmonary tissue (Hiratsuka, et al., J Heart Lung Transplant. 1998 December; 17(12): 1238-46); pancreatic tissue (Bellmann, et al., J Clin Invest. 1995 June; 95(6): 2840-2845), and the like.

Seizure conditions that damage neurons include, e.g., epileptic seizure (Yenari, ibid; Blondeau, et al. Neuroscience 2002, 109(2), 231-241); or chemically induced seizure (Tsuchiya, et al., Neurosurgery, 2003, 53(5), 1179-1187).

Thermal stresses include hyperthermia conditions such as fever, heat stroke, and the like (Barclay and Robertson, J Neurobiol, 2003 56(4), 360-271; Sato, et al., Brain Res, 1996, 740(1-2), 117-123); and hypothermia (Kandor and Goldberg, Proc Natl Acad Sci USA. 1997 May 13; 94(10): 4978-4981).

Aging includes conditions such as atherosclerosis which affects smooth muscle cells (Minowada, G. and Welch, W. J. (1995) J. Clin. Invest. 95:3-12; Johnson, A. J., et al. (1995) Arterio. Thromb. Vasc. Biol. 15(1):27-36).

Other conditions include radiation damage, e.g., from ultraviolet light to tissues such as murine fibroblasts (Simon, M. M., et al. (1995) J. Clin. Res. 95(3): 926-933), and light damage to retinal cells (Yu, et, al, Molecular Vision 2001; 7:48-56).

Trauma includes, for example, mechanical injury, e.g., pressure damage to retinal ganglions in glaucoma (Ishii, et al., Invest Opthalmol Vis Sci, 2003, 44(5), 1982-1992).

Toxic conditions include doses of chemicals or biochemicals, for example, methamphetamine (Malberg & Seiden, Poster "MDMA Administration Induces Expression of HSP70 in the Rat Brain" Society for Neuroscience Annual Meeting, New Orleans, La., October 25-30, 1997); antiretroviral HIV therapeutics (Keswani, et al., Annals Neurology, 2002, 53(1), 57-64); heavy metals, amino acid analogs, chemical oxidants, ethanol, glutamate, and other toxins (Ashburner, M. and Bonner, J. J. (1979) Cell: 17:241-254; Lindquist, S. (1986) Ann. Rev. Biochem. 55:1151-1191; Craig, E. A. (1985) Crit. Rev. Biochem. 18(3):239-280; Morimoto, et al., In: The Biology of Heat Shock Proteins and Molecular Chaperone, (1994) pp. 417-455. Cold Spring Harbor Laboratory Press. Cold Spring Harbor, N.Y.); and the like.

Cystic fibrosis is a genetic disorder which results from a mutation in a single glycoprotein called the cystic fibrosis transmembrane conductance regulator (CFTR). As a result of the mutation, post-translational processing of CFTR cannot proceed correctly and the glycoprotein fails to be delivered to the cell membrane. Induction of Hsp70 has been shown to overcome this defective processing and results in functional CFTR protein on the cell surface (Choo-Kang and Zeitlin, *Am. J. Physiol. Lung Cell Mol. Physiol.* (2001), 281:L58-L68).

Therefore, there is a need for new methods of increasing expression of Hsp70 in order to treat disorders responsive to Hsp70.

Extracellular Hsp70 and membrane bound Hsp70 have been shown to play key roles in activation of the innate immune system. Monocytes have been shown to secrete proinflammatory cytokines in response to soluble Hsp70 protein and membrane bound Hsp70 has been shown to provide a target structure for cytolytic attack by natural killer cell.

Natural killer (NK) cells, a type of white blood cell, are known to be an important component of the body's immune system. Because the defining function of NK cells is spontaneous cytotoxicity without prior immunization, NK cells can be the first line of defense in the immune system, and are believed to play a role in attacking cancer cells and infectious diseases. Many conditions, such as immunodeficiency diseases, aging, toxin exposure, endometriosis, and the like can leave subjects with lowered NK cell activity or dysfunctional NK cells.

For example, subjects can have decreased or deficient NK cell activity, in conditions such as chronic fatigue syndrome (chronic fatigue immune dysfunction syndrome) or Epstein-Barr virus, post viral fatigue syndrome, post-transplantation syndrome or host-graft disease, exposure to drugs such as anticancer agents or nitric oxide synthase inhibitors, natural aging, and various immunodeficiency conditions such as severe combined immunodeficiency, variable immunodeficiency syndrome, and the like. (Caligiuri M, Murray C, Buchwald D, Levine H, Cheney P, Peterson D, Komaroff A L, Ritz J. Phenotypic and functional deficiency of natural killer cells in patients with chronic fatigue syndrome. Journal of Immunology 1987; 139: 3306-13; Morrison L J A, Behan W H M, Behan P O. Changes in natural killer cell phenotype in patients with post-viral fatigue syndrome. Clinical and Experimental Immunology 1991; 83: 441-6; Klingemann, HG Relevance and Potential of Natural Killer Cells in Stem Cell Transplantation Biology of Blood and Marrow Transplantation 2000; 6:90-99; Ruggeri L, Capanni M, Mancusi A, Aversa F, Martelli M F, Velardi A. Natural killer cells as a therapeutic tool in mismatched transplantation. Best Pract Res Clin Haematol. 2004 September; 17(3):427-38; Cifone M G, Ulisse S, Santoni A. Natural killer cells and nitric oxide. Int Immunopharmacol. 2001 August; 1(8):1513-24; Plackett T P, Boehmer E D, Faunce D E, Kovacs E J. Aging and innate immune cells. J Leukoc Biol. 2004 August; 76(2):291-9. Epub 2004 Mar. 23; Alpdogan O, van den Brink M R. IL-7 and IL-15: therapeutic cytokines for immunodeficiency. Trends Immunol. 2005 January; 26(1):56-64; Heusel J W, Ballas Z K. Natural killer cells: emerging concepts in immunity to infection and implications for assessment of immunodeficiency. Curr Opin Pediatr. 2003 December; 15(6):586-93; Hacein-Bey-Abina S, Fischer A, Cavazzana-Calvo M. Gene therapy of X-linked severe combined immunodeficiency. Int J Hematol. 2002 November; 76(4):295-8; Baumert E, Schlesier M, Wolff-Vorbeck G, Peter H H. Alterations in lymphocyte subsets in variable immunodeficiency syndrome Immun Infekt. 1992 July; 20(3):73-5.)

NK cells are known to have activity against a wide range of infectious pathogens such as bacteria, viruses, fungi, protozoan parasites, combined infections, e.g., combined bacterial/viral infections, and the like. NK cells are believed to be particularly important in combating intracellular infections where the pathogens replicate in the subjects cells, e.g., a substantial fraction of viruses and many other pathogens that can form intracellular infections.

For example, a wide range of fungal infections are reported to be targeted by NK cells such as Cryptococcus neoformans, dermatophytes, e.g., Trichophyton rubrum, Candida albicans, Coccidioides immitis, Paracoccidioides brasiliensis, or the like (Hidore M R, Mislan T W, Murphy J W. Responses of murine natural killer cells to binding of the fungal target Cryptococcus neoformans Infect Immun. 1991 April; 59(4): 1489-99; Akiba H, Motoki Y, Satoh M, Iwatsuki K, Kaneko F; Recalcitrant trichophytic granuloma associated with NK-cell deficiency in a SLE patient treated with corticosteroid. Eur J Dermatol. 2001 January-February; 11(1):58-62; Mathews H L, Witek-Janusek L. Antifungal activity of interleukin-2-activated natural killer (NK1.1+) lymphocytes against Candida albicans. J Med Microbiol. 1998 November; 47(11):1007-14; Ampel N M, Bejarano G C, Galgiani J N. Killing of Coccidioides immitis by human peripheral blood mononuclear cells. Infect Immun. 1992 October; 60(10):4200-4; Jimenez B E, Murphy J W. In vitro effects of natural killer cells against Paracoccidioides brasiliensis yeast phase. Infect Immun. 1984 November; 46(2):552-8.)

Also targeted by NK cells are bacteria, especially intracellular bacteria, e.g., Mycobacterium tuberculosis, Mycobacterium avium, Listeria monocytogenes, many different viruses, such as human immunodeficiency virus, herpesviruses, hepatitis, and the like, and viral/bacterial co-infection (Esin S, Batoni G, Kallenius G, Gaines H, Campa M, Svenson S B, Andersson R, Wigzell H. Proliferation of distinct human T cell subsets in response to live, killed or soluble extracts of Mycobacterium tuberculosis and Myco. avium. Clin Exp Immunol. 1996 June; 104(3):419-25; Kaufmann S H. Immunity to intracellular bacteria. Annu Rev Immunol. 1993; 11:129-63; See D M, Khemka P, Sahl L, Bui T, Tilles J G. The role of natural killer cells in viral infections. Scand J Inmuunol. 1997 September; 46(3):217-24; Brenner B G, Dascal A, Margolese R G, Wainberg M A. Natural killer cell function in patients with acquired immunodeficiency syndrome and related diseases. J Leukoc Biol. 1989 July; 46(1): 75-83; Kottilil S. Natural killer cells in HIV-1 infection: role of NK cell-mediated non-cytolytic mechanisms in pathogenesis of HIV-1 infection. Indian J Exp Biol. 2003 November; 41(11):1219-25; Herman R B, Koziel M J. Natural killer cells and hepatitis C: is losing inhibition the key to clearance? Clin Gastroenterol Hepatol. 2004 December; 2(12):1061-3; Beadling C, Slifka M K. How do viral infections predispose patients to bacterial infections? Curr Opin Infect Dis. 2004 June; 17(3):185-91)

In addition, NK cells combat protozoal infections including toxoplasmosis, trypanosomiasis, leishmaniasis and malaria, especially intracellular infections (Korbel D S, Finney O C, Riley E M. Natural killer cells and innate immunity to protozoan pathogens. Int J Parasitol. 2004 December; 34(13-14):1517-28; Ahmed J S, Mehlhom H. Review: the cellular basis of the immunity to and immunopathogenesis of tropical theileriosis. Parasitol Res. 1999 July; 85(7):539-49; Osman M, Lausten S B, El-Sefi T, Boghdadi I, Rashed M Y, Jensen S L. Biliary parasites. Dig Surg. 1998; 15(4):287-96; Gazzinelli R T, Denkers E Y, Sher A. Host resistance to Toxoplasma gondii: model for studying the selective induction of cell-mediated immunity by intracellular parasites. Infect Agents Dis. 1993 June; 2(3): 139-49; Askonas B A, Bancroft G J. Interaction of African trypanosomes with the immune system. Philos Trans R Soc Lond B Biol Sci. 1984 Nov. 13; 307(1131):41-9; Allison A C, Eugui E M. The role of cell-mediated immune responses in resistance to malaria, with special reference to oxidant stress. Annu Rev Immunol. 1983; 1:361-92.)

NK cells have been shown to play a role in attacking cancer cells that present membrane bound Hsp70. It is believed that membrane bound Hsp70 binds to CD94 receptors on the surface of NK cells and cause them to produce and secrete high amounts of the enzyme, granzyme B which is thought to enter the tumor cell via interaction with membrane bound Hsp70 and induce apoptosis (see Radons and Multhoff, Exerc. Immunol. Rev. (2005), 11:17-33). Therefore, there is an urgent need for effective treatments for increasing NK cell activity for the treatment of cancer and other disorders that respond to NK induction.

SUMMARY OF THE INVENTION

It has been reported in U.S. Pat. No. 6,800,660, U.S. Pat. No. 6,762,204, U.S. Pat. No. 7,037,940, U.S. Pat. No. 7,001,923, and U.S. Pat. No. 6,924,312 that certain bis(thio-hydrazide amide) compounds significantly enhance the anticancer activity of taxol and taxol analogs. The entire teachings of these patents are incorporated by reference herein in their entirety. Disclosed herein are methods of purifying these bis(thio-hydrazide amide) compounds.

One embodiment of the present invention is a method of purifying a compound represented by Structural Formula I:

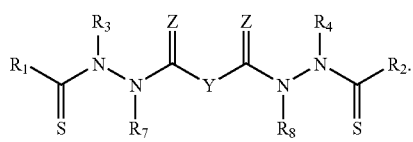

or a tautomer, pharmaceutically acceptable salt, solvate, clathrate, or prodrug thereof, wherein Y is a covalent bond or an optionally substituted straight chained hydrocarbyl group, or, Y, taken together with both >C=Z groups to which it is bonded, is an optionally substituted aromatic group;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic ring optionally fused to an aromatic ring;

$R_7$-$R_8$ are independently —H, an optionally substituted aliphatic group, or an optionally substituted aryl group; and Z is O or S;

comprising dissolving the compound in a solvent consisting of THF-acetone or THF-CH$_3$CN, and precipitating the compound with water.

DETAILED DESCRIPTION OF THE INVENTION

The present invention relates to methods of purifying bis (thio-hydrazide amides) represented by Structural Formula I and pharmaceutically acceptable salts and solvates of the compounds represented by Structural Formula I.

In one embodiment, the compound is dissolved in a solvent selected from the group consisting of THF-acetone, THF-CH$_3$CN, THF, acecotone, CH$_3$CN, THF-EtOH, or acetone-EtOH, and precipitated with water.

In one embodiment, the compound is dissolved in a solvent consisting of THF-acetone or THF-CH$_3$CN, and precipitated with water.

Another embodiment, further comprises dissolving the precipitate in a second solvent selected from the group consisting of THF-acetone, THF-CH$_3$CN, THF, acecotone, CH$_3$CN, THF-EtOH, or acetone-EtOH, and precipitating the compound with water.

Another embodiment, further comprises dissolving the precipitate in a second solvent consisting of THF-acetone or THF-CH$_3$CN, and precipitating the compound with water.

Another embodiment, further comprises washing the precipitate with THF-water.

In another embodiment, the THF-water is in a ratio of 1:3 (v/v).

In another embodiment, the compound, solvent, and water are stirred for 3 to 4 hours.

In another embodiment, the compound, second solvent, and water are stirred for 3 to 4 hours.

In another embodiment, the temperature is 0-4° C.

In one embodiment, the solvent is THF-acetone.

In another embodiment, the solvent is THF-CH$_3$CN.

In one embodiment, the second solvent is THF-acetone.

In one embodiment, the second solvent is THF-CH$_3$CN.

In one embodiment, the solvent is THF-acetone and the second solvent is THF-CH$_3$CN.

In one embodiment, the solvent is THF-CH$_3$CN and the second solvent is THF-acetone.

In one embodiment, the purified compound is at least 96% pure. In one aspect, the compound is at least 97% pure. In one aspect, the compound is at least 98% pure. In one aspect, the compound is at least 99% pure.

In one embodiment, Y in Structural Formula I is a covalent bond, —C($R_5R_6$)—, —(CH$_2$CH$_2$)—, trans-(CH=CH)—, cis-(CH=CH)— or —(C≡C)— group, preferably —C($R_5R_6$)—. $R_1$-$R_4$ are as described above for Structural Formula I. $R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted C2-C6 alkylene group.

In specific embodiments, Y taken together with both >C=Z groups to which it is bonded, is an optionally substituted aromatic group. In this instance, certain bis(thio-hydrazide amides) are represented by Structural Formula II:

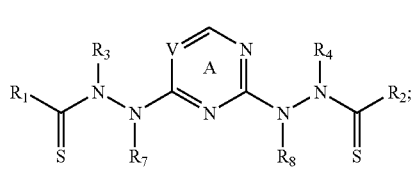

or a tautomer, pharmaceutically acceptable salt, solvate, clathrate, or prodrug thereof, wherein Ring A is substituted or unsubstituted and V is —CH— or —N—. The other variables in Structural Formula II are as described herein for Structural Formula I or IIIa.

In particular embodiments, the bis(thio-hydrazide amides) are represented by Structural Formula IIIa:

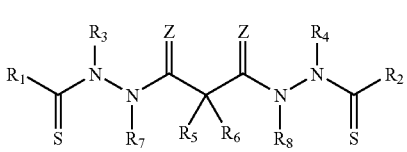

or a tautomer, pharmaceutically acceptable salt, solvate, clathrate, or prodrug thereof, wherein $R_1$-$R_8$ are as described above for Structural Formula I.

In Structural Formulas I-IIIa, $R_1$ and $R_2$ are the same or different and/or $R_3$ and $R_4$ are the same or different; preferably, $R_1$ and $R_2$ are the same and $R_3$ and $R_4$ are the same. In Structural Formulas I and IIIa, Z is preferably O. Typically in Structural Formulas I and IIIa, Z is O; $R_1$ and $R_2$ are the same; and $R_3$ and $R_4$ are the same. More preferably, Z is O; $R_1$ and $R_2$ are the same; $R_3$ and $R_4$ are the same, and $R_7$ and $R_8$ are the same.

In other embodiments, the bis(thio-hydrazide amides) are represented by Structural Formula IIIa: $R_1$ and $R_2$ are each an optionally substituted aryl group, preferably an optionally substituted phenyl group; $R_3$ and $R_4$ are each an optionally substituted aliphatic group, preferably an alkyl group optionally substituted with —OH, halogen, phenyl, benzyl, pyridyl, or C1-C8 alkoxy and $R_6$ is —H or methyl, more preferably, methyl or ethyl group optionally substituted with —OH, halogen, phenyl, benzyl, pyridyl, or C1-C8 alkoxy and $R_6$ is —H or methyl optionally substituted with —OH, halogen or C1-C4 alkoxy; and $R_5$ and $R_6$ are as described above, but $R_5$ is preferably —H and $R_6$ is preferably —H, an aliphatic or substituted aliphatic group.

Alternatively, $R_1$ and $R_2$ are each an optionally substituted aryl group; $R_3$ and $R_4$ are each an optionally substituted aliphatic group; $R_5$ is —H; and $R_6$ is —H, an aliphatic or substituted aliphatic group. Preferably, $R_1$ and $R_2$ are each an optionally substituted aryl group; $R_3$ and $R_4$ are each an alkyl group optionally substituted with —OH, halogen, phenyl, benzyl, pyridyl, or C1-C8 alkoxy and $R_6$ is —H or methyl; and $R_5$ is —H and $R_6$ is —H or methyl. Even more preferably, $R_1$ and $R_2$ are each an optionally substituted phenyl group, preferably optionally substituted with —OH, halogen, C1-4 alkyl or C1-C4 alkoxy; $R_3$ and $R_4$ are each methyl or ethyl optionally substituted with —OH, halogen or C1-C4 alkoxy; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In another embodiment, the bis(thio-hydrazide amides) are represented by Structural Formula IIIa: $R_1$ and $R_2$ are each an optionally substituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula I, preferably both an optionally substituted alkyl group; and $R_5$ and $R_6$ are as described above, but $R_5$ is preferably —H and $R_6$ is preferably —H, an aliphatic or substituted aliphatic group, more preferably —H or methyl.

Alternatively, the bis(thio-hydrazide amides) are represented by Structural Formula IIIa: $R_1$ and $R_2$ are each an optionally substituted aliphatic group; $R_3$ and $R_4$ are as described above for Structural Formula I, preferably both an optionally substituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula I, preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group group optionally substituted with —OH, halogen, phenyl, benzyl, pyridyl, or C1-C8 alkoxy and $R_6$ is —H or methyl; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl optionally substituted with —OH, halogen or C1-C4 alkoxy; and $R_5$ is —H and $R_6$ is —H or methyl.

In particular embodiments, the bis(thio-hydrazide amides) are represented by Structural Formula IIIb:

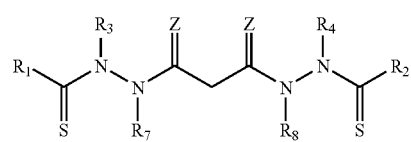

or a tautomer, pharmaceutically acceptable salt, solvate, clathrate, or prodrug thereof, wherein $R_1$, $R_2$, $R_3$, $R_4$, $R_7$, $R_8$, and Z are as defined above for Structural Formula IIIa.

In specific embodiments, the bis(thio-hydrazide amides) are represented by Structural Formula IVa:

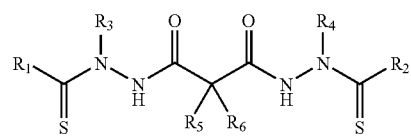

or a tautomer, pharmaceutically acceptable salt, solvate, clathrate, or prodrug thereof, wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-dimethoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and R$_4$ are both methyl, and R$_5$ and R$_6$ are both —H; R$_1$ and R$_2$ are both 2,3-dimethoxyphenyl, R$_3$ and R$_4$ are both methyl, R$_5$ is methyl, and R$_6$ is —H; R$_1$ and R$_2$ are both 2,5-difluorophenyl, R$_3$ and R$_4$ are both methyl, and R$_5$ and R$_6$ are both —H; R$_1$ and R$_2$ are both 2,5-difluorophenyl, R$_3$ and R$_4$ are both methyl, R$_5$ is methyl, and R$_6$ is —H; R$_1$ and R$_2$ are both 2,5-dichlorophenyl, R$_3$ and R$_4$ are both methyl, and R$_5$ and R$_6$ are both —H; R$_1$ and R$_2$ are both 2,5-dimethylphenyl, R$_3$ and R$_4$ are both methyl, and R$_5$ and R$_6$ are both —H; R$_1$ and R$_2$ are both 2,5-dimethoxyphenyl, R$_3$ and R$_4$ are both methyl, and R$_5$ and R$_6$ are both —H; R$_1$ and R$_2$ are both phenyl, R$_3$ and R$_4$ are both methyl, and R$_5$ and R$_6$ are both —H; R$_1$ and R$_2$ are both 2,5-dimethoxyphenyl, R$_3$ and R$_4$ are both methyl, R$_5$ is methyl, and R$_6$ is —H; R$_1$ and R$_2$ are both cyclopropyl, R$_3$ and R$_4$ are both methyl, and R$_5$ and R$_6$ are both —H; R$_1$ and R$_2$ are both cyclopropyl, R$_3$ and R$_4$ are both ethyl, and R$_5$ and R$_6$ are both —H; R$_1$ and R$_2$ are both cyclopropyl, R$_3$ and R$_4$ are both methyl, R$_5$ is methyl, and R$_6$ is —H; R$_1$ and R$_2$ are both 1-methylcyclopropyl, R$_3$ and R$_4$ are both methyl, and R$_5$ and R$_6$ are both —H; R$_1$ and R$_2$ are both 1-methylcyclopropyl, R$_3$ and R$_4$ are both methyl, R$_5$ is methyl and R$_6$ is —H; R$_1$ and R$_2$ are both 1-methylcyclopropyl, R$_3$ and R$_4$ are both methyl, R$_5$ is ethyl, and R$_6$ is —H; R$_1$ and R$_2$ are both 1-methylcyclopropyl, R$_3$ and R$_4$ are both methyl, R$_5$ is n-propyl, and R$_6$ is —H; R$_1$ and R$_2$ are both 1-methylcyclopropyl, R$_3$ and R$_4$ are both methyl, and R$_5$ and R$_6$ are both methyl; R$_1$ and R$_2$ are both 1-methylcyclopropyl, R$_3$ and R$_4$ are both ethyl, and R$_5$ and R$_6$ are both —H; R$_1$ and R$_2$ are both 1-methylcyclopropyl, R$_3$ is methyl, R$_4$ is ethyl, and R$_5$ and R$_6$ are both —H; R$_1$ and R$_2$ are both 2-methylcyclopropyl, R$_3$ and R$_4$ are both methyl, and R$_5$ and R$_6$ are both —H; R$_1$ and R$_2$ are both 2-phenylcyclopropyl, R$_3$ and R$_4$ are both methyl, and R$_5$ and R$_6$ are both —H; R$_1$ and R$_2$ are both 1-phenylcyclopropyl, R$_3$ and R$_4$ are both methyl, and R$_5$ and R$_6$ are both —H; R$_1$ and R$_2$ are both cyclobutyl, R$_3$ and R$_4$ are both methyl, and R$_5$ and R$_6$ are both —H; R$_1$ and R$_2$ are both cyclopentyl, R$_3$ and R$_4$ are both methyl, and R$_5$ and R$_6$ are both —H; R$_1$ and R$_2$ are both cyclohexyl, R$_3$ and R$_4$ are both methyl, and R$_5$ and R$_6$ are both —H; R$_1$ and R$_2$ are both cyclohexyl, R$_3$ and R$_4$ are both phenyl, and R$_5$ and R$_6$ are both —H; R$_1$ and R$_2$ are both methyl, R$_3$ and R$_4$ are both methyl, and R$_5$ and R$_6$ are both —H; R$_1$ and R$_2$ are both methyl, R$_3$ and R$_4$ are both t-butyl, and R$_5$ and R$_6$ are both —H; R$_1$ and R$_2$ are both methyl, R$_3$ and R$_4$ are both phenyl, and R$_5$ and R$_6$ are both —H; R$_1$ and R$_2$ are both t-butyl, R$_3$ and R$_4$ are both methyl, and R$_5$ and R$_6$ are both —H; R$_1$ and R$_2$ are ethyl, R$_3$ and R$_4$ are both methyl, and R$_5$ and R$_6$ are both —H; or R$_1$ and R$_2$ are both n-propyl, R$_3$ and R$_4$ are both methyl, and R$_5$ and R$_6$ are both —H.

In particular embodiments, the bis(thio-hydrazide amides) are represented by Structural Formula IVb:

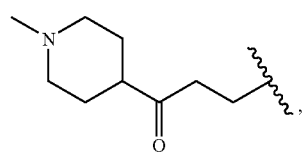

IVb or a tautomer, pharmaceutically acceptable salt, solvate, clathrate, or prodrug thereof, wherein R$_1$, R$_2$, R$_3$, and R$_4$ are as defined above for Structural Formula IVa.

In specific embodiments, the bis(thio-hydrazide amides) are represented by Structural Formula V:

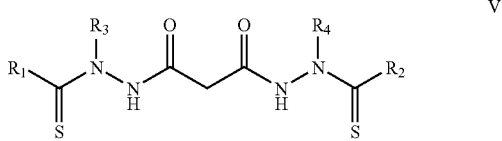

V or a tautomer, pharmaceutically acceptable salt, solvate, clathrate, or prodrug thereof, wherein: R$_1$ and R$_2$ are both phenyl, and R$_3$ and R$_4$ are both o-CH$_3$-phenyl; R$_1$ and R$_2$ are both o-CH$_3$C(O)O-phenyl, and R$_3$ and R$_4$ are phenyl; R$_1$ and R$_2$ are both phenyl, and R$_3$ and R$_4$ are both methyl; R$_1$ and R$_2$ are both phenyl, and R$_3$ and R$_4$ are both ethyl; R$_1$ and R$_2$ are both phenyl, and R$_3$ and R$_4$ are both n-propyl; R$_1$ and R$_2$ are both p-cyanophenyl, and R$_3$ and R$_4$ are both methyl; R$_1$ and R$_2$ are both p-nitro phenyl, and R$_3$ and R$_4$ are both methyl; R$_1$ and R$_2$ are both 2,5-dimethoxyphenyl, and R$_3$ and R$_4$ are both methyl; R$_1$ and R$_2$ are both phenyl, and R$_3$ and R$_4$ are both n-butyl; R$_1$ and R$_2$ are both p-chlorophenyl, and R$_3$ and R$_4$ are both methyl; R$_1$ and R$_2$ are both 3-nitrophenyl, and R$_3$ and R$_4$ are both methyl; R$_1$ and R$_2$ are both 3-cyanophenyl, and R$_3$ and R$_4$ are both methyl; R$_1$ and R$_2$ are both 3-fluorophenyl, and R$_3$ and R$_4$ are both methyl; R$_1$ and R$_2$ are both 2-furanyl, and R$_3$ and R$_4$ are both phenyl; R$_1$ and R$_2$ are both 2-methoxyphenyl, and R$_3$ and R$_4$ are both methyl; R$_1$ and R$_2$ are both 3-methoxyphenyl, and R$_3$ and R$_4$ are both methyl; R$_1$ and R$_2$ are both 2,3-dimethoxyphenyl, and R$_3$ and R$_4$ are both methyl; R$_1$ and R$_2$ are both 2-methoxy-5-chlorophenyl, and R$_3$ and R$_4$ are both ethyl; R$_1$ and R$_2$ are both 2,5-difluorophenyl, and R$_3$ and R$_4$ are both methyl; R$_1$ and R$_2$ are both 2,5-dichlorophenyl, and R$_3$ and R$_4$ are both methyl; R$_1$ and R$_2$ are both 2,5-dimethylphenyl, and R$_3$ and R$_4$ are both methyl; R$_1$ and R$_2$ are both 2-methoxy-5-chlorophenyl, and R$_3$ and R$_4$ are both methyl; R$_1$ and R$_2$ are both 3,6-dimethoxyphenyl, and R$_3$ and R$_4$ are both methyl; R$_1$ and R$_2$ are both phenyl, and R$_3$ and R$_4$ are both 2-ethylphenyl; R$_1$ and R$_2$ are both 2-methyl-5-pyridyl, and R$_3$ and R$_4$ are both methyl; or R$_1$ is phenyl; R$_2$ is 2,5-dimethoxyphenyl, and R$_3$ and R$_4$ are both methyl; R$_1$ and R$_2$ are both methyl, and R$_3$ and R$_4$ are both p-CF$_3$-phenyl; R$_1$ and R$_2$ are both methyl, and R$_3$ and R$_4$ are both o-CH$_3$-phenyl; R$_1$ and R$_2$ are both —(CH$_2$)$_3$COOH; and R$_3$ and R$_4$ are both phenyl; R$_1$ and R$_2$ are both represented by the following structural formula:

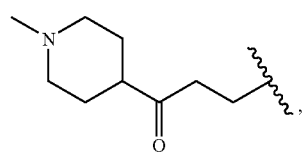

and R$_3$ and R$_4$ are both phenyl; R$_1$ and R$_2$ are both n-butyl, and R$_3$ and R$_4$ are both phenyl; R$_1$ and R$_2$ are both n-pentyl, R$_3$ and R$_4$ are both phenyl; R$_1$ and R$_2$ are both methyl, and R$_3$ and R$_4$ are both 2-pyridyl; R$_1$ and R$_2$ are both cyclohexyl, and R$_3$ and R$_4$ are both phenyl; R$_1$ and R$_2$ are both methyl, and R$_3$ and R$_4$ are both 2-ethylphenyl; R$_1$ and R$_2$ are both methyl, and R$_3$ and R$_4$ are both 2,6-dichlorophenyl; R$_1$-R$_4$ are all methyl; R$_1$ and R$_2$ are both methyl, and R$_3$ and R$_4$ are both t-butyl; R$_1$ and R$_2$ are both ethyl, and R$_3$ and R$_4$ are both methyl; R$_1$ and R$_2$ are both t-butyl, and R$_3$ and R$_4$ are both methyl; R$_1$ and R$_2$ are both cyclopropyl, and R$_3$ and R$_4$ are both methyl; R$_1$ and R$_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

Preferred examples of bis(thio-hydrazide amides) include Compounds (1)-(18) and pharmaceutically acceptable salts and solvates thereof:

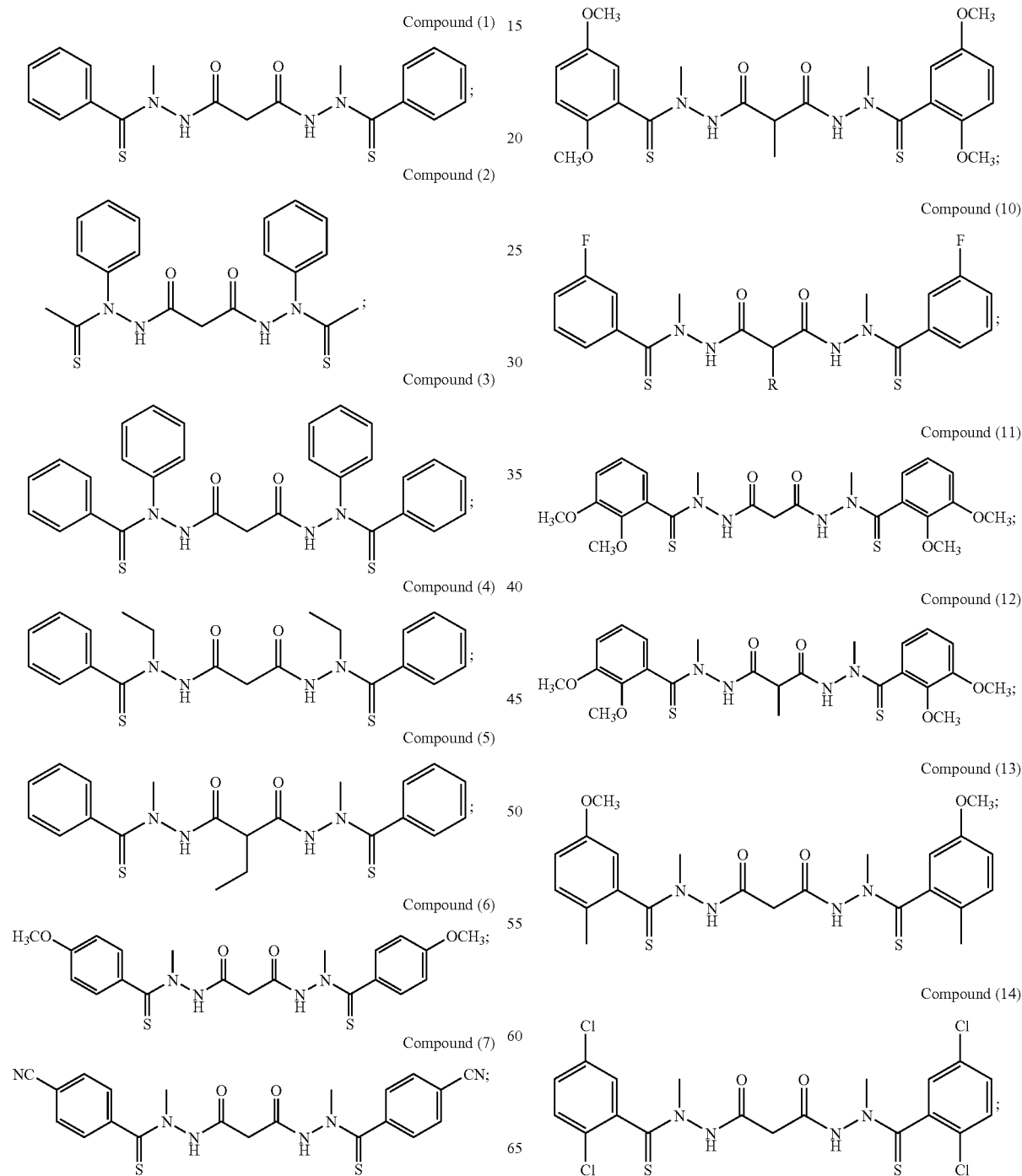

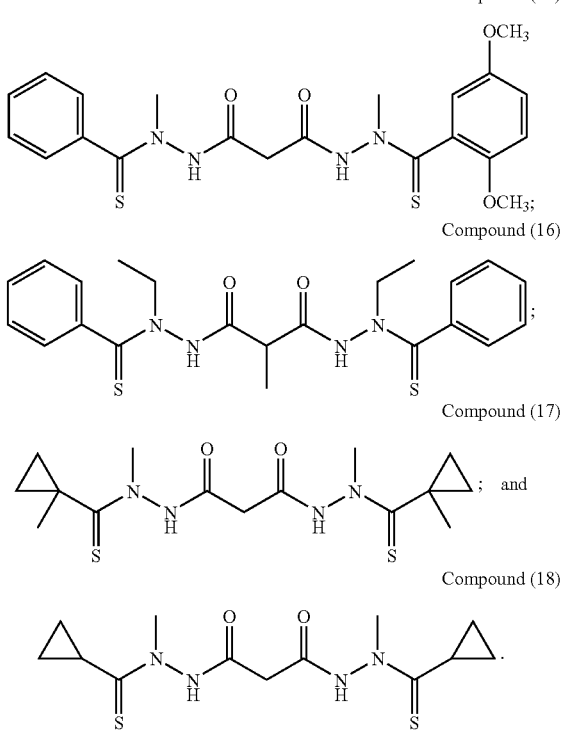

Compound (15)

Compound (16)

Compound (17)

Compound (18)

As used herein, the term "bis(thio-hydrazide amide)" and references to the Structural Formulas of this invention also include pharmaceutically acceptable salts and solvates of these compounds and Structural Formulas. Examples of acceptable salts and solvates are described in US Publication No.: 20060135595 and U.S. patent application Ser. No. 11/432,307 filed 11 May 2006, titled Synthesis Of Bis(Thio-Hydrazide Amide) Salts, the entire contents of each of which are incorporated herein by reference.

It is to be understood when one tautomeric form of a disclosed compound is depicted structurally, other tautomeric forms are also encompassed.

Certain compounds of the invention may be obtained as different stereoisomers (e.g., diastereomers and enantiomers). The invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

An "alkyl group" is saturated straight or branched chain linear or cyclic hydrocarbon group. Typically, a straight chained or branched alkyl group has from 1 to about 20 carbon atoms, preferably from 1 to about 10, and a cyclic alkyl group has from 3 to about 10 carbon atoms, preferably from 3 to about 8. An alkyl group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group. Suitable substituents for an alkyl group are those which do not substantially interfere with the anti-cancer activity of the disclosed compounds. Suitable substituents are as described below for aliphatic groups. Preferred substituents on alkyl groups include, —OH, —NH$_2$, —NO$_2$, —CN, —COOH, halogen, aryl, C1-C8 alkoxy, C1-C8 haloalkoxy and —CO (C1-C8 alkyl). More preferred substituents on alkyl groups include —OH, halogen, phenyl, benzyl, pyridyl, and C1-C8 alkoxy. More preferred substituents on alkyl groups include —OH, halogen, and C1-C4 alkoxy.

A "straight chained hydrocarbyl group" is an alkylene group, i.e., —(CH$_2$)$_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N (R$^a$)—), wherein R$^a$ is defined below. A preferred linkage group is —C(R$_5$R$_6$)—, wherein R$_5$ and R$_6$ are defined above. Suitable substitutents for an alkylene group and a hydrocarbyl group are those which do not substantially interfere with the anti-cancer activity of the disclosed compounds. R$_5$ and R$_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahydrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —$R^a$, —OH, —Br, —Cl, —I, —F, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NR^cCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^dH$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$.

$R^a$-$R^d$ are each independently an alkyl group, aromatic group, non-aromatic heterocyclic group or —$N(R^aR^b)$, taken together, form a non-aromatic heterocyclic group. The alkyl, aromatic and non-aromatic heterocyclic group represented by $R^a$-$R^d$ and the non-aromatic heterocyclic group represented by —$N(R^aR^b)$ are each optionally and independently substituted with one or more groups represented by $R^\#$. Preferably $R^a$-$R^d$ are unsubstituted.

$R^\#$ is $R^+$, —$OR^+$, —O(haloalkyl), —$SR^+$, —$NO_2$, —CN, —NCS, —$N(R^+)_2$, —$NHCO_2R^+$, —NHC(O)$R^+$, —NHNHC(O)$R^+$, —NHC(O)N($R^+$)$_2$, —NHNHC(O)N($R^+$)$_2$, —$NHNHCO_2R^+$, —C(O)C(O)$R^+$, —C(O)$CH_2$C(O)$R^+$, —$CO_2R^+$, —C(O)$R^+$, —C(O)N($R^+$)$_2$, —OC(O)$R^+$, —OC(O)N($R^+$)$_2$, —S(O)$_2R^+$, —$SO_2N(R^+)_2$, —S(O)$R^+$, —$NHSO_2N(R^+)_2$, —$NHSO_2R^+$, —C(=S)N($R^+$)$_2$, or —C(=NH)—N($R^+$)$_2$.

$R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —$NO_2$, amine, alkylamine or dialkylamine. Preferably $R^+$ is unsubstituted. Optionally, the group —$N(R^+)_2$ is a non-aromatic heterocyclic group, provided that non-aromatic heterocyclic groups represented by $R^+$ and —$N(R^+)_2$ that comprise a secondary ring amine are optionally acylated or alkylated.

Preferred substituents for a phenyl group, including phenyl groups represented by $R_1$-$R_4$, include C1-C4 alkyl, C1-C4 alkoxy, C1-C4 haloalkyl, C1-C4 haloalkoxy, phenyl, benzyl, pyridyl, —OH, —$NH_2$, —F, —Cl, —Br, —I, —$NO_2$ or —CN. More preferred for a phenyl group, including phenyl groups represented by $R_1$-$R_4$, include $R_1$ and $R_2$ are optionally substituted with —OH, —CN, halogen, C1-4 alkyl or C1-C4 alkoxy Preferred substituents for a cycloalkyl group, including cycloalkyl groups represented by $R_1$ and $R_2$, are alkyl groups, such as a methyl or ethyl group.

The bis(thio-hydrazide amide) disclosed herein can be prepared by the methods described in U.S. Publication Nos. 20060135595, 2003/0045518 and 2003/0119914, U.S. application Ser. No. 11/432,307, filed 11 May 2006, titled Synthesis Of Bis(Thio-Hydrazide Amide) Salts, U.S. Provisional Patent No. 60/708,977 filed 16 Aug. 2005, titled Bis(Thio-Hydrazide Amide) Formulation and also according to methods described in U.S. Publication No. 2004/0225016 A1, entitled TREATMENT FOR CANCERS. The entire teachings of these applications are incorporated herein by reference.

The present invention is illustrated by the following examples, which are not intended to be limiting in any way.

EXAMPLE 1

Purification of Compound 1

Compound 1 used in the following purification procedures was prepared by the following procedure. 274.3 kg of RO/DI water was added to a reactor (10° C.). 5.475 g of NaOH pellets were added until a clear solution was obtained. 28.35 kg of S-(thiobenzoyl)thioglycolic acid was added to the reactor (0-5° C.). 7.965 kg of methylhydrazine was added to the reactor while stirring (0-10° C.). The reactor temperature was increased to 20.0° C. over 150 minutes. The precipitate of thiobenzoyl-$N^1$-methylhydrazide (19.05 kg) was collected.

18.95 kg of thiobenzoyl-$N^1$-methylhydrazide was added to a reactor and 221.6 kg of anhydrous ethyl acetate was added with stirring. After the material was dissolved, the reactor was cooled to 4.0° C. 12.13 kg of TEA was added to the reactor, followed by a solution of malonyl chloride (9.30 kg) in anyhydrous ethyl acetate (34.0 kg) (−5 to 10° C.). The reactor temperature was increased to 11.4° C. over 95 min. 96.15 kg of RO/DI water was added (2.5° C.+/−2.5° C.) and stirred for 20 min. NaCl solution (11.430 kg in 19.07 kg RO/DI water) was added in two portions (draining aqueous layer after each addition) and stirred (27 min, 19 min). The organic layer was washed with ACS ethyl acetate. Ethyl acetate was removed by distillation at 100+/−50 mm Hg (23-28° C.). The cake was washed with ethyl acetate. The product was dried under vacuum and N-malonyl-bis(N'-methyl-N'-thiobenzoylhydrazide) (15.233 kg) was collected.

Purification procedure (THF-$CH_3CN$—$H_2O$): To a solution of Compound 1 (2 g, 95%) in THF (20 ml) was added $CH_3CN$ (6 ml), cooled to 0-4° C. To the mixture was added cold water (0-4° C., 60 ml) with stirring. The whole solution was stirred for 3 h followed by filtration. The precipitate was washed with cold THF-$H_2O$ (1:3, v/v), and dried to give Compound 1 (1.8 g, 98%).

Purification procedure (THF-Acetone-$H_2O$): To a solution of Compound 1 (2 g, 95%) in THF (20 ml) was added acetone (6 ml), cooled to 0-4° C. To the mixture was added cold water (0-4° C., 60 ml) with stirring. The whole solution was stirred for 3 hr, and filtered. The precipitate was washed with cold THF-$H_2O$ (1:3), and dried to give Compound 1 in a yield and purity similar to the method described above.

99+% pure Compound 1 was obtained by combination of the above two procedures sequentially.

The data from purification procedures with Compound 1 is provided in Tables 1 and 2.

TABLE 1

| # | Solvent | Comp #1 | Time | T (° C.) | Purity (230 nM) % | Impurity % | Purity (254 nM) % | Impurity % | Recovery % |
|---|---|---|---|---|---|---|---|---|---|
| 1 | ETOH (5.5 mL) | 0.55 g | 3-4 h | RT | 95.5 | 3.7 | 96.7 | 2.4 | 87 (0.48 g) |
| 2 | MeOH (5.5 mL) | 0.55 g | 3-4 h | RT | 96.7 | 3.0 | 97.3 | 2.1 | 73 (0.4 g) |
| 3 | THF-Acetone-Water (265 mL) | 5 g | 3-4 h | 0-4 | 96.8 | 2.3 | 97.5 | 1.5 | >91 |
| 4 | THF-Acetone-Water (265 mL) THF-Water washing | 5 g | 3-4 h | 0-4 | 96.9 | 1.98 | 97.9 | 1.38 | 91 (4.6 g) |
| 5 | THF-Acetone-Water & THF-CH₃CN-Water | 1 g | 3-4 h | 0-4 | 97.8 | 1.3 | 98.3 | 0.8 | >82 |
| 6 | THF-Acetone-Water & THF-CH₃CN-Water THF-Water Washing | 1 g | 3-4 h | 0-4 | 97.8 | 1.5 | 98.8 | 0.7 | 82 |
| 7 | THF-CH₃CN-Water | 5 g | 3-4 h | 0-4 | 97.3 | 2.0 | 98.0 | 1.3 | >90 |
| 8 | THF-CH₃CN-Water THF-Water Washing | 5 g | 3-4 h | 0-4 | 97.8 | 1.9 | 98.1 | 1.2 | 90 (4.5 g) |
| 9 | THF-CH₃CN-Water (less volume 86 mL) | 2 g | 3-4 h | 0-4 | 97.8 | 1.7 | 98.3 | 1.0 | >90 |
| 10 | THF-CH₃CN-Water (less volume) THF-Water Washing | 2 g | 3-4 h | 0-4 | 98.1 | 1.6 | 98.5 | 0.95 | 90 |
| 11 | THF-Acetone-Water (less volume) THF-Water washing | 2 g | 3-4 h | 0-4 | 98.0 | 1.6 | 98.3 | 1.0 | 90 (1.8 g) |

TABLE 2

| Exp. | SM mmol | Solvent | Conc. mM | T (° C.) | Hours | Recovery (%) | Purity (%) 254; 230 nm | Imp. (%) 254; 230 nm |
|---|---|---|---|---|---|---|---|---|
| 1 | 12.5 | THF-acetone-H₂O | 48 | 0-4 | 4 | 91 | 97.5; 96.8 | 1.5; 2.3 |
| 2 | 12.5 | THF-acetone- H₂O With THF- H₂O washing | 48 | 0-4 | 4 | 91 | 97.9; 96.9 | 1.38; 1.98 |
| 3 | 2.5 | Expt. 4 plus THF-CH₃CN—H₂O | 48 | 0-4 | 4 | 82 | 98.3; 97.8 | 0.8; 1.3 |
| 4 | 2.5 | Expt. 4 plus THF-CH₃CN—H₂O With THF- H₂O washing | 48 | 0-4 | 4 | 82 | 98.8; 97.8 | 0.7; 1.5 |
| 5 | 12.5 | THF-CH₃CN—H₂O | 48 | 0-4 | 4 | 90 | 98.0; 97.3 | 1.3; 2.0 |
| 6 | 12.5 | THF-CH₃CN—H₂O With THF- H₂O washing | 48 | 0-4 | 4 | 90 | 98.1; 97.8 | 1.2 |
| 7 | 5 | THF-CH₃CN—H₂O* | 48 | 0-4 | 4 | 90 | 98.3; 97.8 | 1.0; 1.7 |
| 8 | 5 | THF-CH₃CN—H₂O* With THF-H₂O washing | 48 | 0-4 | 4 | 90 | 98.5; 98.1 | 0.95; 1.6 |
| 9 | 5 | THF-acetone- H₂O* With THF- H₂O washing | 48 | 0-4 | 4 | 90 | 98.3; 98.0 | 1.0; 1.6 |
| 10 | 2.5 | Expt. 8 plus Expt. 9 | 48 | 0-4 | 4 | 90 | 99.2; 99.5 | 0.43; 0.35 |
| 11 | 1.8 | Expt. 8 plus Expt. 9* | 48 | 0-4 | 4 | 85 | 99.3; 99.4 | 0.35; 0.33 |

*with less water

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of purifying a compound represented by the following Structural Formula:

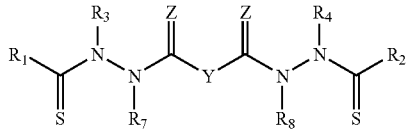

wherein:

Y is a covalent bond or an optionally substituted straight chained hydrocarbyl group, or, Y, taken together with both >C=Z groups to which it is bonded, is an optionally substituted aromatic group;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;

$R_7$-$R_8$ are independently —H, an optionally substituted aliphatic group, or an optionally substituted aryl group; and Z is O or S;

comprising dissolving the compound in a solvent selected from the group consisting of THF-acetone, THF-$CH_3CN$, THF, acectone, $CH_3CN$, THF-EtOH, or acetone-EtOH, and precipitating the compound with water.

2. The method of claim 1, further comprising washing the precipitate with THF-water.

3. The method of claim 2, wherein the THF-water is in a ratio of 1:3 (v/v).

4. The method of claim 1, wherein the compound, solvent, and water are stirred for 3 to 4 hours.

5. The method of claim 4, wherein the temperature is 0-4° C.

6. The method of claim 1 or 2, further comprising dissolving the precipitate in a second solvent selected from the group consisting of THF-acetone, THF-$CH_3CN$, THF, acectone, $CH_3CN$, THF-EtOH, or acetone-EtOH, and precipitating the compound with water.

7. The method of claim 6, further comprising washing the precipitate with THF-water.

8. The method of claim 7, wherein the THF-water is in a ratio of 1:3 (v/v).

9. The method of claim 6, wherein the compound, second solvent, and water are stirred for 3 to 4 hours.

10. The method of claim 9, wherein the temperature is 0-4° C.

11. The method of claim 1, wherein the compound is represented by the following Structural Formula:

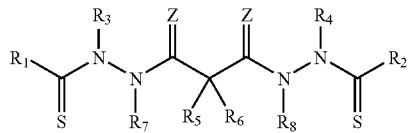

wherein:

$R_7$-$R_8$ are both —H, and:

$R_1$ and $R_2$ are both phenyl, $R_3$ and $R_4$ are both methyl, and $R_5$ and $R_6$ are both —H;

$R_1$ and $R_2$ are both phenyl, $R_3$ and $R_4$ are both ethyl, and $R_5$ and $R_6$ are both —H;

$R_1$ and $R_2$ are both 4-cyanophenyl, $R_3$ and $R_4$ are both methyl, $R_5$ is methyl, and $R_6$ is —H;

$R_1$ and $R_2$ are both 4-methoxyphenyl, $R_3$ and $R_4$ are both methyl, and $R_5$ and $R_6$ are both —H;

$R_1$ and $R_2$ are both phenyl, $R_3$ and $R_4$ are both methyl, $R_5$ is methyl, and $R_6$ is —H;

$R_1$ and $R_2$ are both phenyl, $R_3$ and $R_4$ are both ethyl, $R_5$ is methyl, and $R_6$ is —H;

$R_1$ and $R_2$ are both 4-cyanophenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, $R_5$ is methyl, and $R_6$ is —H;

$R_1$ and $R_2$ are both 3-cyanophenyl, $R_3$ and $R_4$ are both methyl, and $R_5$ and $R_6$ are both —H;

$R_1$ and $R_2$ are both 3-fluorophenyl, $R_3$ and $R_4$ are both methyl, and $R_5$ and $R_6$ are both —H;

$R_1$ and $R_2$ are both 4-chlorophenyl, $R_3$ and $R_4$ are both methyl, $R_5$ is methyl, and $R_6$ is —H;

$R_1$ and $R_2$ are both 2-dimethoxyphenyl, $R_3$ and $R_4$ are both methyl, and $R_5$ and $R_6$ are both —H;

$R_1$ and $R_2$ are both 3-methoxyphenyl, $R_3$ and $R_4$ are both methyl, and $R_5$ and $R_6$ are both —H;

$R_1$ and $R_2$ are both 2,3-dimethoxyphenyl, $R_3$ and $R_5$ are both methyl, and $R_5$ and $R_6$ are both —H;

$R_1$ and $R_2$ are both 2,3-dimethoxyphenyl, $R_3$ and $R_4$ are both methyl, $R_5$ is methyl, and $R_6$ is —H;

$R_1$ and $R_2$ are both 2,5-difluorophenyl, $R_3$ and $R_4$ are both methyl, and $R_5$ and $R_6$ are both —H;

$R_1$ and $R_2$ are both 2,5-difluorophenyl, $R_3$ and $R_4$ are both methyl, $R_5$ is methyl, and $R_6$ is —H;

$R_1$ and $R_2$ are both 2,5-dichlorophenyl, $R_3$ and $R_4$ are both methyl, and $R_5$ and $R_6$ are both —H;

$R_1$ and $R_2$ are both 2,5-dimethylphenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, and $R_5$ and $R_6$ are both —H;

$R_1$ and $R_2$ are both phenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, $R_5$ is methyl, and $R_6$ is —H;

$R_1$ and $R_2$ are both cyclopropyl, $R_3$ and $R_4$ are both methyl, and $R_5$ and $R_6$ are both —H;

$R_1$ and $R_2$ are both cyclopropyl, $R_3$ and $R_4$ are both ethyl, and $R_5$ and $R_6$ are both —H;

$R_1$ and $R_2$ are both cyclopropyl, $R_3$ and $R_4$ are both methyl, $R_5$ is methyl, and $R_6$ is —H;

$R_1$ and $R_2$ are both 1-methylcyclopropyl, $R_3$ and $R_4$ are both methyl, and $R_5$ and are both —H;

$R_1$ and $R_2$ are both 1-methylcyclopropyl, $R_3$ and $R_4$ are both methyl, $R_5$ is methyl and $R_6$ is —H;

$R_1$ and $R_2$ are both 1-methylcyclopropyl, $R_3$ and $R_4$ are both methyl, $R_5$ is ethyl, and $R_6$ is —H;

$R_1$ and $R_2$ are both 1-methylcyclopropyl, $R_3$ and $R_4$ are both methyl, $R_5$ is n-propyl, and $R_6$ is —H;

$R_1$ and $R_2$ are both 1-methylcyclopropyl, $R_3$ and $R_4$ are both methyl, and $R_5$ and $R_6$ are both methyl;

$R_1$ and $R_2$ are both 1-methylcyclopropyl, $R_3$ and $R_4$ are both ethyl, and $R_5$ and $R_6$ are both —H;

$R_1$ and $R_2$ are both 1-methylcyclopropyl, $R_3$ is methyl, $R_4$ is ethyl, and $R_5$ and $R_6$ are both —H;

$R_1$ and $R_2$ are both 2-methylcyclopropyl, $R_3$ and $R_4$ are both methyl, and $R_5$ and $R_6$ are both —H;

$R_1$ and $R_2$ are both 2-phenylcyclopropyl, $R_3$ and $R_4$ are both methyl, and $R_5$ and $R_6$ are both —H;

$R_1$ and $R_2$ are both 1-phenylcyclopropyl, $R_3$ and $R_4$ are both methyl, and $R_5$ and $R_6$ are both —H;

$R_1$ and $R_2$ are both cyclobutyl, $R_3$ and $R_4$ are both methyl, and $R_5$ and $R_6$ are both —H;

$R_1$ and $R_2$ are both cyclopentyl, $R_3$ and $R_4$ are both methyl, and $R_5$ and $R_6$ are both —H;

$R_1$ and $R_2$ are both cyclohexyl, $R_3$ and $R_4$ are both methyl, and $R_5$ and $R_6$ are both —H;

$R_1$ and $R_2$ are both cyclohexyl, $R_3$ and $R_4$ are both phenyl, and $R_5$ and $R_6$ are both —H;

$R_1$ and $R_2$ are both methyl, $R_3$ and $R_4$ are both methyl, and $R_5$ and $R_6$ are both —H;

$R_1$ and $R_2$ are both methyl, $R_3$ and $R_4$ are both t-butyl, and $R_5$ and $R_6$ are both —H;

$R_1$ and $R_2$ are both methyl, $R_3$ and $R_4$ are both phenyl, and $R_5$ and $R_6$ are both —H;

$R_1$ and $R_2$ are both t-butyl, $R_3$ and $R_4$ are both methyl, and $R_5$ and $R_6$ are both —H;

$R_1$ and $R_2$ are ethyl, $R_3$ and $R_4$ are both methyl, and $R_5$ and $R_6$ are both —H; or $R_1$ and $R_{2\ are}$ both n-propyl, $R_3$ and $R_4$ are both methyl, and $R_5$ and $R_6$ are both —H.

12. The method of claim 1, wherein the compound is represented by the following Structural Formula:

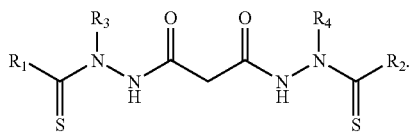

13. The method of claim 1, wherein the compound is represented by one of the following Structural Formulas:

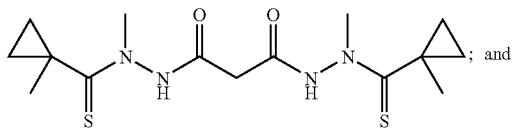; and

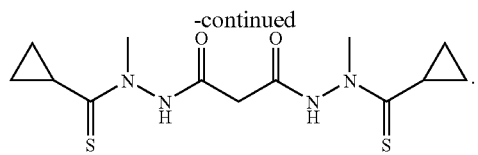.

14. A method of purifying a compound represented by the following Structural Formula:

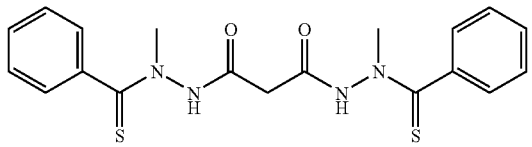

comprising dissolving the compound in a solvent selected from the group consisting of THF-acetone or THF-CH$_3$CN, and precipitating the compound with water.

15. The method of claim 14, further comprising washing the precipitate with THF-water.

16. The method of claim 15, wherein the THF-water is in a ratio of 1:3 (v/v).

17. The method of claim 14, wherein the compound, solvent, and water are stirred for 3 to 4 hours.

18. The method of claim 17, wherein the temperature is 0-4° C.

19. The method of claim 14 or 15, further comprising dissolving the precipitate in a second solvent selected from the group consisting of THF-acetone or THF-CH$_3$CN, and precipitating the compound with water.

20. The method of claim 19, further comprising washing the precipitate with THF-water.

21. The method of claim 20, wherein the THF-water is in a ratio of 1:3 (v/v).

22. The method of claim 19, wherein the compound, second solvent, and water are stirred for 3 to 4 hours.

23. The method of claim 22, wherein the temperature is 0-4° C.

24. The method of claim 14, wherein the solvent is THF-acetone.

25. The method of claim 14, wherein the solvent is THF-CH$_3$CN.

26. The method of claim 19, wherein the second solvent is THF-acetone.

27. The method of claim 19, wherein the second solvent is THF-CH$_3$CN.

28. The method of claim 19, wherein the solvent is THF-acetone and the second solvent is THF-CH$_3$CN.

29. The method of claim 19, wherein the solvent is THF-CH$_3$CN and the second solvent is THF-acetone.

* * * * *

UNITED STATES PATENT AND TRADEMARK OFFICE
CERTIFICATE OF CORRECTION

| | | |
|---|---|---|
| PATENT NO. | : 7,645,904 B2 | Page 1 of 1 |
| APPLICATION NO. | : 11/901265 | |
| DATED | : January 12, 2010 | |
| INVENTOR(S) | : Shoujun Chen et al. | |

It is certified that error appears in the above-identified patent and that said Letters Patent is hereby corrected as shown below:

In column 20, claim 11, line 39, please delete "$R_3$ and $R_5$" and replace with -- $R_3$ and $R_4$ --;

In column 20, claim 11, line 65, please delete "and $R_5$ and" and replace with -- and $R_5$ and $R_6$ --;

In column 21, claim 11, line 35, please delete "$R_1$ and $R_{2\,are}$" and replace with -- $R_1$ and $R_2$ are --.

Signed and Sealed this

Twentieth Day of April, 2010

David J. Kappos
*Director of the United States Patent and Trademark Office*